(12) United States Patent
Kim et al.

(10) Patent No.: US 10,898,535 B2
(45) Date of Patent: Jan. 26, 2021

(54) COMPOSITION FOR INHIBITING AND PREVENTING MYOPATHY, CONTAINING BEAN LEAF EXTRACT AS ACTIVE INGREDIENT

(71) Applicant: AMOREPACIFIC CORPORATION, Seoul (KR)

(72) Inventors: Byung Gyu Kim, Yongin-si (KR); Young-Gyu Kang, Yongin-si (KR); Soo Hyun Kim, Yongin-si (KR); Chan Woong Park, Yongin-si (KR); Hee Young Jeon, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/567,512

(22) Filed: Sep. 11, 2019

(65) Prior Publication Data

US 2020/0000867 A1 Jan. 2, 2020

Related U.S. Application Data

(63) Continuation of application No. 15/580,565, filed as application No. PCT/KR2016/004828 on May 9, 2016, now abandoned.

(30) Foreign Application Priority Data

Jun. 30, 2015 (KR) ........................ 10-2015-0092701

(51) Int. Cl.
| | |
|---|---|
| *A61K 36/48* | (2006.01) |
| *A61Q 19/00* | (2006.01) |
| *A61K 8/9789* | (2017.01) |
| *A61P 21/00* | (2006.01) |
| *A61K 8/96* | (2006.01) |

(52) U.S. Cl.
CPC ................ *A61K 36/48* (2013.01); *A61K 8/96* (2013.01); *A61K 8/9789* (2017.08); *A61P 21/00* (2018.01); *A61Q 19/00* (2013.01); *A61K 2236/39* (2013.01); *A61K 2236/51* (2013.01)

(58) Field of Classification Search
None
See application file for complete search history.

(56) References Cited

U.S. PATENT DOCUMENTS

| 2004/0047927 A1 | 3/2004 | Liu |
| 2010/0056470 A1* | 3/2010 | Taylor ................. C07H 15/256 514/54 |
| 2012/0225054 A1 | 9/2012 | Chen et al. |
| 2012/0238515 A1 | 9/2012 | Pan et al. |
| 2013/0090377 A1 | 4/2013 | Jeon et al. |
| 2015/0150157 A1 | 5/2015 | Maeda et al. |
| 2016/0089359 A1 | 3/2016 | Jung et al. |

FOREIGN PATENT DOCUMENTS

| CN | 102600316 A | | 7/2012 |
| CN | 106176837 | * | 8/2016 |
| JP | 2007063135 A | | 3/2007 |
| JP | 2013507361 A | | 3/2013 |
| KR | 20060066564 A | | 6/2006 |
| KR | 20070117151 A | | 12/2007 |
| KR | 101034596 B1 | | 5/2011 |
| KR | 20110110053 A | | 10/2011 |
| KR | 20120022085 A | | 3/2012 |
| KR | 20140034964 A | | 3/2014 |
| KR | 101439783 B1 | | 9/2014 |
| KR | 20140131881 A | | 11/2014 |

OTHER PUBLICATIONS

Katsuya Hirasaka, "Molecular Nutritional Study on Prevention of Muscle Atrophy", Japan Soc Nutr Food Sci, , 2014, pp. 291-297, vol. 67, Japan.
Satoshi, "Role of Exercise and Nutritional Intake in Prevention of Sarcopenia", Official Journal of The Japan Society for Biomedical Gerontology, 2011, vol. 35, Issue 3, pp. 23-27.
Ho et al., "Difference in flavonoid and isoflavone profile between soybean and soy leaf", Biomed Pharmacotherapy, 2002, vol. 56, pp. 289-295.
Verhoeven et al., "Long-term leucine supplementation does not increase muscle mass or strength in healthy elderly men1-3", AM J Clin Nutr, 2009, vol. 89, pp. 1468-1475.
International Search Report for International Application No. PCT/KR2016/004828 (dated Aug. 25, 2015) (2 Pages).
Dog et al., "Assessing safety of herbal products for menopausal complaints: An international perspective", MATURITAS, 2010, vol. 66, No. 4, pp. 355-362.
Arbogast et al., "Bowman-Birk inhibitor concentrate prevents atrophy, weakness, and oxidative stress in soleus muscle of hindlimb-unloaded mice", J of Applied Physiology, 2007, vol. 102, No. 3, pp. 956-964.
Jiang Yinhua, "Observation of curative effect of external application of pigeon leaf extract on stage III pressure ulcer", China Science and Technology of Traditional Chinese Medicine, 2014, p. 531, vol. 21 No. 5.

* cited by examiner

*Primary Examiner* — Ralph J Gitomer
(74) *Attorney, Agent, or Firm* — Lucas & Mercanti, LLP

(57) ABSTRACT

The present invention relates to a composition for inhibiting and preventing myopathy comprising a bean leaf extract as an active ingredient. More specifically, the composition has an effect of inhibiting the overexpression of Atrogin1 and Murf1 specifically expressed in myocyte and restoring cell activity of myocyte to inhibit and prevent muscle loss by including the extract of bean leaf at stage R6 to R8 during the growth stage of bean.

8 Claims, 4 Drawing Sheets

COMPOSITION FOR INHIBITING AND PREVENTING MYOPATHY, CONTAINING BEAN LEAF EXTRACT AS ACTIVE INGREDIENT

CROSS-REFERENCE TO RELATED APPLICATIONS

This application is a continuation of U.S. patent application Ser. No. 15/580,565 filed Dec. 7, 2017, which is a 371 of PCT/KR2016/004828, filed May 9, 2016, which claims the benefit of Korean Patent Application No. 10-2015-0092701, filed Jun. 30, 2015 the contents of each of which are incorporated herein by reference.

TECHNICAL FIELD

The present invention relates to a composition for inhibiting and preventing myopathy comprising bean leaf extract as an active ingredient, which can be usefully utilized in the field of preparing food, pharmaceutical or cosmetic composition for myopathy.

BACKGROUND ART

Human muscles grow and become strong until the age of 30 after the birth of human, but after 30 years of age, muscle density and function gradually begin to weaken. In particular, if there is no consistent physical exercise, after 30 years of age, the amount of muscle is reduced by 3 to 5% every 10 years. And even if the exercise continues, a certain degree of muscle loss occurs. Most of these muscle losses are a phenomenon mainly caused by aging, but the detailed mechanism of such a phenomenon has various aspects.

Unlike muscle loss due to normal simple aging, sarcopenia by the pathological aspect directly induces muscle weakness and increases the risk of falls or fractures, also causes an outbreak of myopathy and decrease and impairment in various body functions, and increases risk of diabetes and cardiovascular diseases by 8.2 times or more, thereby generally increasing risk of death.

Therefore, it has been considered that the inhibition and prevention of muscle loss is one of the important challenges directly linked to improvement and prevention of various other organically related muscular diseases as well as to general health problems. Also, at present, the population of Korea is rapidly aging due to the decrease in fertility rate and the extension of average life expectancy, and in particular, according to the data of the Korean National Statistical Office in 2010, the elderly population aged 65 or older is expected to reach 15.7% in 2020 and 24.1% in 2030 compared to 9.1% in 2005. This increase corresponds to the fastest growth rate among OECD countries and is also classified as an urgent challenge in terms of social welfare.

According to this trend, many studies are under way to inhibit and prevent muscle loss. Among them, the representative study is the study related to branched-chain amino acid (BCAA) containing leucine, one of the essential amino acids that make up muscles. However, according to this study, leucine was reported to have little effect on skeletal muscle mass changes in the elderly. Thus, it is expected that this study will be difficult to become a fundamental solution of the sarcopenia.

Meanwhile, recently, specific functions of Atrogin1 and Murf1 have been elucidated with regard to the sarcopenia, and they are attracting attention. The Atrogin1 and Murf1 are ubiquitin ligases specifically expressed in myocyte, and this increase in expression is known to cause muscle loss due to ubiquitination and proteasome-dependent degradation of muscle proteins.

In the process of finding ways to solve muscle loss from a new perspective, the present inventors have found that using a composition comprising a bean leaf extract as an active ingredient in relation to the above mechanism has a considerable effect on the inhibition of muscle loss, and thus completed the present invention.

PRIOR ART LITERATURE

Formulations for prevention or treatment of obesity, hyperlipidemia, arteriosclerosis, fatty liver, diabetes mellitus or metabolic syndrome comprising extracts of *Glycine max* leaves as an active ingredient (Korean Patent Laid-Open No. 10-2012-0022085).

Technical Problem

In order to solve the above problems, it is an object of the present invention to provide a composition for inhibiting and preventing myopathy which comprises an bean leaf extract as an active ingredient.

More particularly, it is an object of the present invention to provide a substance capable of inhibiting and preventing muscle loss.

In addition, it is another object of the present invention to provide a food composition, a pharmaceutical composition or a cosmetic composition for inhibiting and preventing myopathy comprising naturally derived extract of bean leaf, which is easy to obtain and has minimal side effects, as an active ingredient.

Technical Solution

In order to achieve the above object, the present invention provides a composition for inhibiting and preventing myopathy comprising a bean leaf extract as an active ingredient.

The bean leaf extract may be an extract of bean leaf at stage R6 to R8 during the growth stages of bean.

The bean leaf extract may be at least one selected from the group consisting of a raw extract of bean leaf, and a fraction, a dried product, a dried fraction, a fermented product and a concentrate thereof.

The composition can be utilized in the form of food, pharmaceutical or cosmetic composition.

Advantageous Effects

The present invention provides a composition capable of inhibiting and preventing myopathy through the solution of the above problem.

More specifically, the present invention provides a substance capable of directly or indirectly inhibiting and preventing muscle loss by providing a substance capable of improving or preventing various myopathy which comprises an extract of bean leaf as an active ingredient.

The bean leaf extract is a natural component, has few side effects on the human body and is easy to obtain. In addition it is economical to prepare because it is made by fully utilizing bean leaf that has not been used industrially in the prior art.

DETAILED DESCRIPTION OF THE INVENTION

Figure 1:
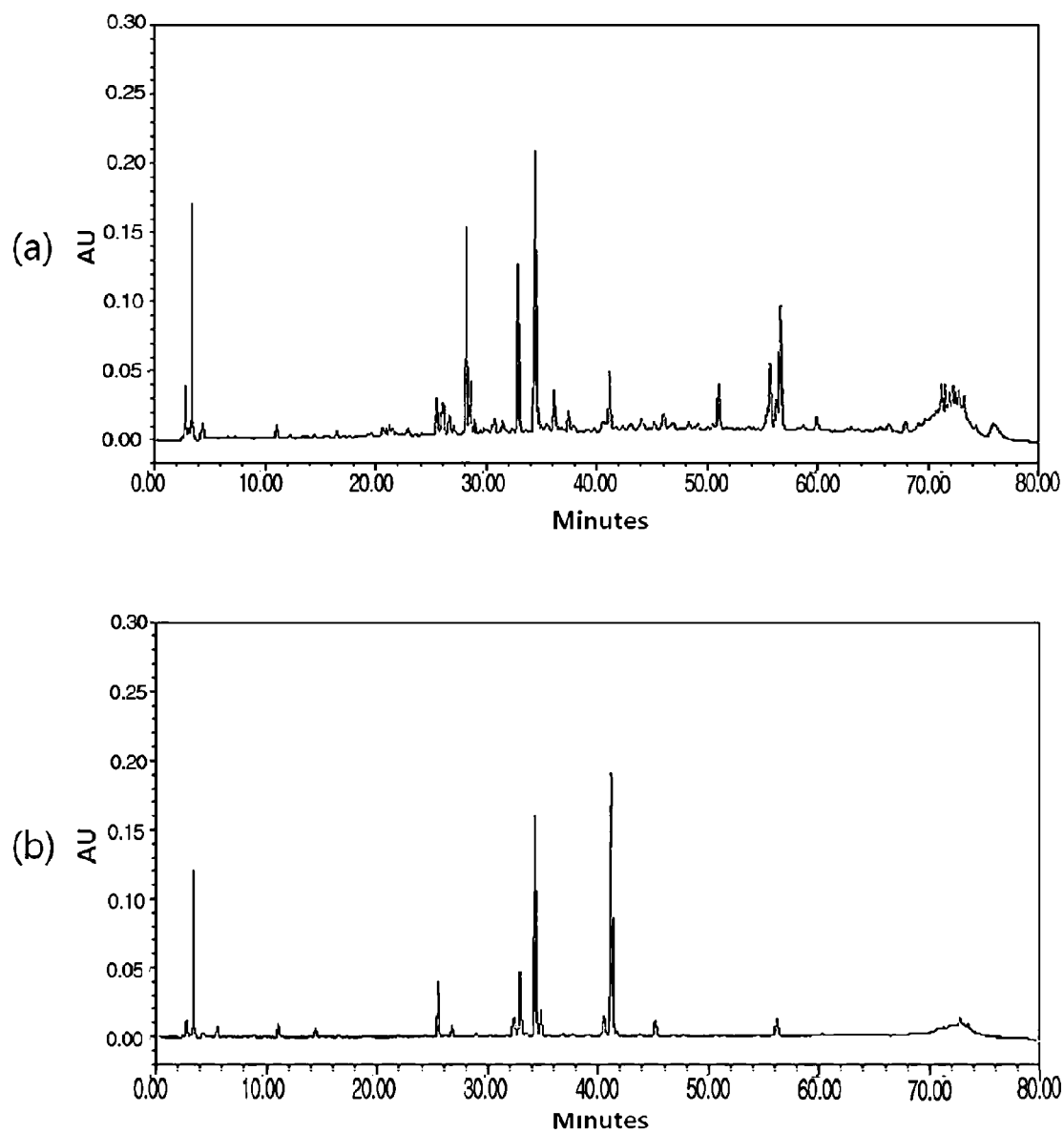
FIG. 1 shows the results of comparative analysis of components of (a) bean leaf extract and (b) bean extract by using HPLC.

The present invention provides a composition for inhibiting and preventing myopathy comprising a bean leaf extract as an active ingredient.

The term "myopathy" used herein should be understood to include at least all of the myopathies directly or indirectly related to the expression of the Atrogin1 or Murf1 protein as described below. The term "myopathy" refers to, but is not limited to, all myopathies, which are accompanied by, or directly or indirectly related mainly to sarcopenia, muscle loss and amyotrophic diseases.

Hereinafter, the contents of the present invention will be described in more detail. It is to be understood, however, that the following describes only the most representative embodiments in order to facilitate understanding of the present invention, and the scope of the present invention is not limited thereto, and covers the entire scope equivalent to the following.

In the present invention, the term "bean" is not limited in its kind and may be, for example, but is not limited to, at least one selected from the group consisting of *Rhynchosia Nolubilis, Glycine max*(L.) Merr., *Vicia faba, Phaseolus vulgaris, Phaseolus vulgaris* L., *Vigna angularis, Phaseolus angularis* W. F. WIGHT., *Pisum sativum* L. and *Glycine max* MERR. In addition, shape of the bean can be any form suitable for extracting the active ingredient.

However, an object of extraction in the present invention is limited to "bean leaf." The reason for this is that, as shown in Example 1 and FIG. 1 to be described later, the constituents of bean and bean leaf are different to each other. And the effect of inhibition and prevention of the myopathy is significant in the bean leaf extract compared with the bean extract. In addition, the present invention is economical and easy to prepare because it can utilize the bean leaf which are conventionally less industrially utilized and discarded.

In order to enhance the inhibition and prevention of myopathy, the bean leaf extract is an extract of bean leaf corresponding to any one of stage R6 to R8 during the whole growth stage of bean as follows.

Stage VE: 1 to 2 Weeks after seeding. Cotyledons emerge from the soil

Stage VC: The cotyledons spread out, one node of stem grows on it, and outer leaves are come into.

Stage V1: One node is generated from the first outer leaves and three leaves are created.

Stage V2: One node is further created at the stage V1 and three leaves are further created.

Stage V3: One node is further created at the stage V2 and three leaves are further created.

Stage V4: One node is further created at the stage V3 and three leaves are further created.

Stage R2: A state where the flowers of bean are in full bloom.

Stage R4: A state where the creation of bean pods is completed.

Stage R5: A state where beans are formed in the bean pods.

Stage R6: A state where green beans have been produced in the bean pods.

Stage R7: A state where the bean pods and beans turn yellow.

Stage R8: A state where the bean pods and beans become completely yellow as the leaves fall.

The bean leaf extract at stage R7 to R8 is preferable, and the bean leaf extract at stage R7 is more preferable. The bean leaf at stage R7 to R8 are sometimes referred to as "autumn bean leaf" because they are bean leaf at a stage in which the color of the leaf changes to yellow.

In this specification, the term "extract" means a component substance extracted from the natural material, regardless of the extraction method, the extraction solvent, the extracted components or the form of the extract. For example, the extract is a broad concept, including all the extract, for example, extracts of components dissolved in a solvent from natural materials using water or an organic solvent, and those obtained by extracting only a specific component of the natural material, i.e., a specific component such as oil and also includes all of the substances obtained by, for example, processing after extraction. Specifically, the extract of the present invention may be at least a form selected from the group consisting of extract of raw bean leaf, additional processed or fermented or enzymatically treated fractions, dried products, dried fractions, fermented products and concentrates.

The method of obtaining the bean leaf extract of the present invention is not limited to any particular method as long as it is a commonly used method in the art. For example, the bean leaf extract can be normally obtained by the method comprising placing the powder of washed, dried and pulverized bean leaves in water or organic solvent, separating the residue and filtrate after extraction and precipitation by filtration and centrifugation, and concentrating the separated filtrate under reduced pressure.

A solvent for the extraction may be at least one selected from water, ethanol, methanol, butanol, ether, ethyl acetate, chloroform or a mixture of these organic solvents and water. And it is preferable to use water or ethanol having a concentration of 30 to 70% in consideration of the safety of raw materials. It is effective to use a mixture of each filtrate obtained through repeated extraction. For example, after obtaining the first extract from ethanol as described above, ethyl acetate was added to the residue to obtain the second extract, and further extraction was repeated once or twice for the residue from the previous step, and then the filtrates of the extracts thus obtained are mixed.

After obtaining the extract, a liquid substance therefrom can be obtained by chilling at room temperature, heating and filtration which are conventional methods known in the art, or the process of evaporating, spray drying or lyophilizing the solvent may be further performed.

There is no particular limitation on the concentration of extract. However, referring to Example 2 or Experimental Examples 1 and 2 to be described later, the effect is usually sufficient at around 100 ppm. And specifically, various concentrations are available depending on the symptom and degree of the disease and the mode of providing the composition.

The bean leaf extract of the present invention inhibits expression or activity of ubiquitin ligase of skeletal muscle to inhibit and prevent myopathy. Generally, the ubiquitin ligase in the human body is an enzyme that induces degradation of the protein by attaching ubiquitin to the surface of the protein to be destroyed as a kind of death signal. In particular, there are ubiquitin ligases, called Atrogin1 and Murf1, which are specifically expressed when the skeletal muscle is reduced. However, unlike conventional ubiquitin ligases that induce the death of unnecessary proteins, the Atrogin1 and Murf1 tend to be overexpressed in patients with myopathy accompanied mainly by pathological muscle loss or atrophy and are now known to be one of the direct molecular biologic causes that cause the sarcopenia. When the Atrogin1 and Murf1 are overexpressed, the degradation pathway is activated too much as compared with the synthesis of myocyte, and thus normal myocyte loss occurs.

In connection with the above mechanism, the bean leaf extract of the present invention may prevent muscle loss and may further improve and prevent other myopathy organically associated therewith by inhibiting the overexpression of the Atrogin1 and Murf1 genes.

Considering that the majority of muscle loss diseases are classified as a type of degenerative disease in accordance to aging, the composition of the present invention can be positively utilized for a senior group.

The composition of the present invention may be provided in any one formulation of food, pharmaceutical and cosmetic compositions.

The food composition of the present invention, which is one form of utilization, is mainly a composition of a health functional food, may contain the bean leaf extract as an active ingredient and may be blended into a conventional food composition as it is or with other food or a component of such food. There is no particular limitation on the type of the above-mentioned food and the food may include beverages, tea, drinks, alcoholic beverages, vitamin complexes and the like and they may be used in any form that is commonly recognized.

The pharmaceutical composition of the present invention, which is another form of utilization, includes the bean leaf extract as an active ingredient and may further include at least one other pharmaceutically acceptable carrier. For example, saline, sterile water, Ringer's solution, buffered saline, dextrose solution, maltodextrin solution, glycerol, ethanol or a mixture of two or more thereof can be used, and other conventional additives such as an antioxidant, a buffer, a bacteriostatic agent and the like may be added as needed.

The pharmaceutical composition can be formulated in injectable formulation such as aqueous solutions, suspensions, emulsions and the like or oral formulation by additionally adding diluents, dispersants, surfactants, binders and lubricants.

The dosage formulation for oral administration may be at least one selected from the group consisting of tablets, pills, granules, fine granules, pulvis, powders, soft capsules, hard capsules, emulsions, syrups, and drinks.

The cosmetic composition of the present invention, which is still another form of utilization, includes the bean leaf extract as an active ingredient and may further comprise the other functional additives and all components which may be included in the general cosmetic composition.

The functional additive may be any one or more of, for example, water-soluble vitamins, oil-soluble vitamins, polymer peptides, polymeric polysaccharides, sphingolipids and seaweed extracts. Also, if necessary, it is possible to additionally add oil and fat components, moisturizers, emollient agents, surfactants, organic and inorganic pigments, organic powder, ultraviolet absorbers, antiseptics, bactericides, antioxidants, plant extracts, pH adjusting agents, alcohol, coloring matters, flavoring agents, blood circulation promoting agents, cool-feeling agents, antiperspirant agents, purified water and the like.

The formulation of the cosmetic composition can be appropriately selected according to application characteristics, and may be, for example, in the formulation of skin lotion, skin softener, skin toner, astringent, lotion, milk lotion, moisturizing lotion, nutrition lotion, massage cream, nutrition cream, moisturizing cream, hand cream, foundation, powder, essence, nutritional essence, pack, soap, cleansing foam, cleansing lotion, cleansing cream, body lotion and body cleanser, spray and the like.

Hereinafter, Examples 1 to 2 and Experimental Examples 1 to 2 according to the present invention are described. The following Examples and Experimental Examples are only examples related to the practice and effect of the present invention, and the scope and effect of the present invention are not limited thereto.

Example 1: Comparison of Components of Bean Leaf Extract and Bean Extract

To confirm that constituents of bean leaf extract and bean extract are not the same, component analysis using HPLC (high performance liquid chromatography) was performed.

HPLC Analysis Condition

The bean leaf extract and the bean extract were dissolved in 70% ethanol to make 10,000 ppm solution. Thereafter, HPLC (Waters 2695 model) was used and component analysis was performed using a detector (Waters 2996 PDA detector). The stationary phase was a Mightysil RP-18 GP 250-4.6 (5 μm) column from Kanto Chemical Co., and the mobile phase was a mixture of water and 0.1% acetic acid solution to acetonitrile.

HPLC Analysis Result

The results of the HPLC component analysis are shown in FIG. In FIG. 1, (a) is the bean leaf extract and (b) is the bean extract.

According to FIG. 1, the bean leaf extract and the bean extract exhibit different separation patterns. It can be clearly seen that the peaks appear to be totally different at each time point, and thus the constituents of the bean extract and the bean leaf extract are not the same with each other.

Example 2: Preparation of Bean Leaf Extract

Each of bean leaf collected at the growing stage (stage VC/V2/V4/R2/R4/R6/R7, 7 stages in total) was washed with purified water, dried and then pulverized. 100 g of the powder of bean leaf was added to 1 liter of a 70% by weight aqueous ethanol solution, extracted at room temperature (25° C.) for 12 hours, and then filtered through a 300-mesh filter cloth.

The extract was put into a 3 liters separatory funnel, and 1 liter of ethyl acetate was added, and thereafter stirred to mix while shaking, and then take the upper layer (ethyl acetate layer) when completely separated into two layers. The lower layer is extracted twice again with a separatory funnel. Each of the separated upper layers was combined and concentrated under reduced pressure to 50 by using a distillation apparatus equipped with a cooling condenser and dried. Thus, extracts of bean leaves of each step were combined to give 10.3 g.

Experimental Example 1: Evaluation for Ability to Recover Cell Activity of Myocyte In the present Experimental Example 1, the experiments were conducted to evaluate the recovery efficacy of the bean leaf extract on the decrease in cell activity of myocyte in a model of muscle loss induced by Dexamethasone.

Dexamethasone is a kind of glucocorticoid, and increases expression of the Atrogin1 and Murf1 in vitro and in vivo to accelerate proteolytic degradation, thereby resulting in decrease in skeletal muscle, induction of myocyte death, and reduction of cell activity. Accordingly, an experimental model of dexamethasone to myocyte is a useful model for evaluating the function of sarcopenia and is widely used.

The C2C12 (mouse myoblast) used in Experimental Example 1 was purchased from American Type Culture Collection (Manassas, Va., USA) and the cells were cultured in DMEM containing 10% FBS, 100 units/mL Penicillin, and 100 mg/mL streptomycin. Specific experimental methods are as follows.

First, to prepare the experimental group, C2C12 was plated on a 12-well plate and cultured until the cells were confluent at 80 to 90% of the plate. Subsequently, the differentiation of the cells was induced by exchanging with 2% horse serum and DMEM medium. After the medium was changed and then cultivation was further performed for 5 to 7 days to complete the differentiation of the cells, the final concentration of dexamethasone was adjusted to 1 μM. At the same time, the extracts of bean leaves at stage VC/V2/V4/R2/R4/R6/R7 obtained in Example 2 were adjusted to a final concentration of 100 ppm.

Meanwhile, as a control group, the cells without any treatment other than dexamethasone were used, and as a comparison group, the cells treated with dexibuprofen at a final concentration of 100 μM instead of the extracts of bean leaf, which is known to be effective for suppressing inflammation and effective for muscle pain, were used.

After 24 hours of treatment with the material, the medium was replaced with medium containing 10% solution of CCK8 (cholecystokinin 8), and allowed to react for 10 minutes, and the cell activity was measured by measuring the absorbance at 450 nm. To increase the reliability, each sample was repeatedly measured three times to derive the average value.

Figure 2:
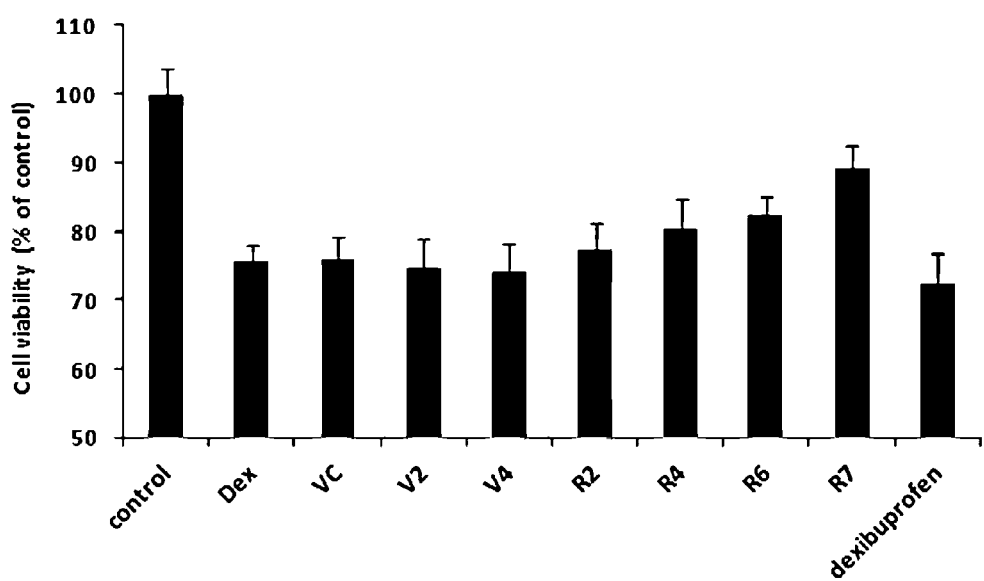
FIG. 2 is a graph showing relative cell activity (%) of the experimental group, the control group and the comparison group in comparison with the normal myocyte (control).

The results of the experiment are shown in FIG. 2 and Table 1 below.

TABLE 1

| Treatment | Experimental group | | | | | | | Comparison group |
|---|---|---|---|---|---|---|---|---|
| material | VC | V2 | V4 | R2 | R4 | R6 | R7 | Dexibuprofen |
| Change in cell activity relative to control group (%) | 0.4 | −1.3 | −2.0 | 2.5 | 6.2 | 9.1 | 18.1 | −4.1 |

FIG. 2 is a graph showing relative cell activities of experimental group, control group (Dex) and comparison group (dexibuprofen) relative normal myocyte (control). Table 1 shows change in cell activity of the experimental group and the comparison group relative to the control group.

Referring to FIG. 2, it is confirmed that the control group treated with the dexamethasone has decreased myocyte activity in comparison with the normal myocyte. Compared with this control group, the experimental group treated with the bean leaf extracts shows that the activity of myocyte is restored as a whole.

Specifically, as shown in Table 1, the experimental groups treated with the extract of bean leaf at stage R4 to R7 show a significant increase in the activity of myocyte by 6.2 to 18.1% compared to the control group. Especially, the extract of bean leaf at stage R7 shows very effective cell activity recovery.

Thus, it is confirmed that the bean leaf extract of the present invention has inhibition and prevention efficacy of muscle loss.

Meanwhile, in the group treated with the dexibuprofen as a comparison group, no recovery of myocyte activity is observed, and thus it can be seen that common muscle soreness inhibitors are not suitable for inhibition or prevention of muscle loss, and their mechanisms of action are also different with each other.

Experimental Example 2: Evaluation of Inhibition of Expression of Atrogin1 and Murf1 Gene (mRNA)

In the present Experimental Example 2, experiments were conducted to evaluate the inhibitory efficacy of the bean leaf extract against the overexpression of Atrogin1 and Murf1 mRNA in the muscle loss induced model by dexamethasone.

The experimental group, the control group and the comparison group of Experimental Example 2 were prepared in the same manner as Experimental Example 1.

Provided that, when 6 hours had elapsed since the treatment with each final material, RNA was extracted with trizol reagent (TRIzol agent, Invitrogen) after washing twice with cold saline, Subsequently, cDNA was synthesized using 1 μg/μl of the extracted and quantified RNA and a reverse transcription system (Promega). Expression patterns of each gene were measured using primers and probes (Applied biosystems) previously designed for genes of the synthesized cDNA and Atrogin1, Murf1, and GAPD. At this time, polymerase chain reaction (PCR) and analysis were performed using a Rotor-Gene 3000 system (Corbett Research, Sydney, Australia). To increase the reliability, each sample was repeatedly measured three times to derive the average value.

Figure 3:
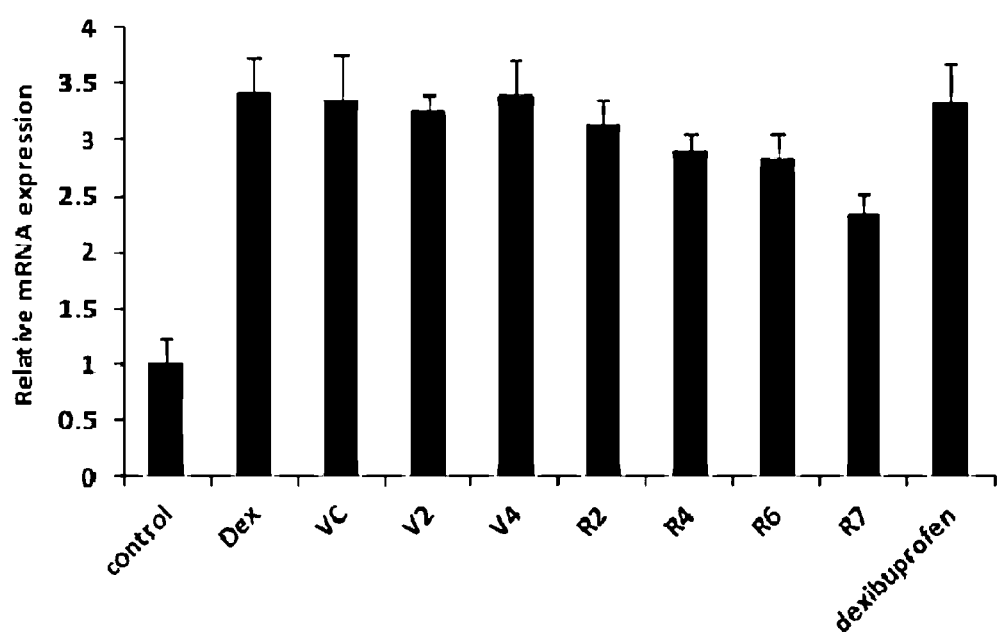
FIG. 3 is a graph showing relative expression amounts (%) of Atrogin1 gene (mRNA) of the experimental group, the control group and the comparison group in comparison with normal myocyte (control).
Figure 4:
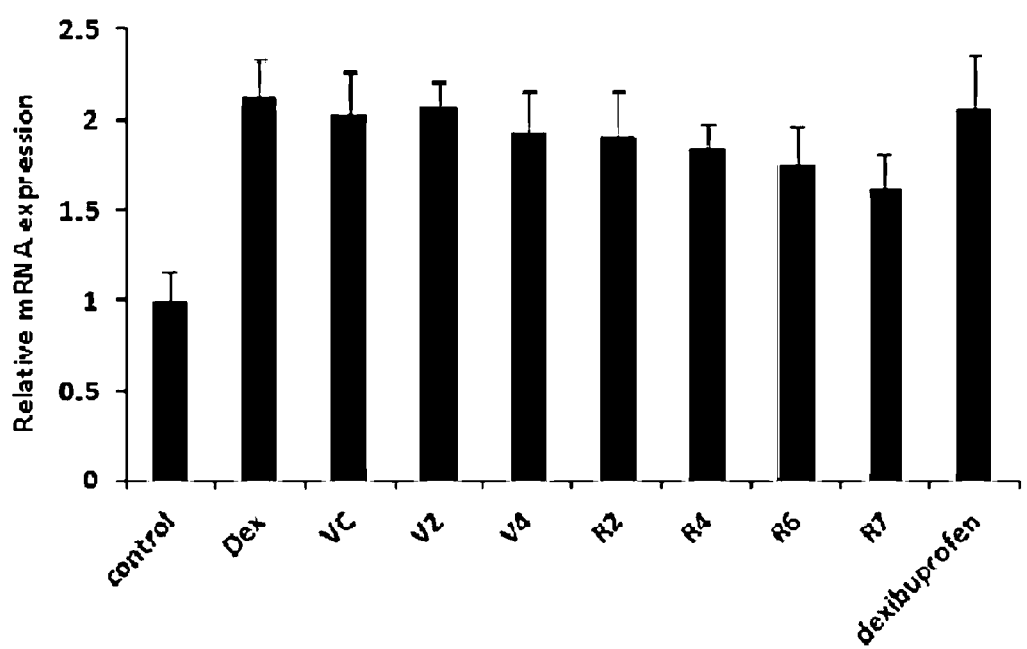
FIG. 4 is a graph showing relative expression amounts (%) of Murf1 gene (mRNA) of the experimental group, the control group and the comparison group in comparison with normal myocyte (control).

The experimental results are shown in FIGS. 3 and 4 and Table 2 and Table 3 below.

TABLE 2

| Treatment | Experimental group | | | | | | | Comparison group |
|---|---|---|---|---|---|---|---|---|
| material | VC | V2 | V4 | R2 | R4 | R6 | R7 | Dexibuprofen |
| Change in Atrogin1 gene expression relative to control group (%) | −2.0 | −4.7 | −0.6 | −8.2 | −14.9 | −16.2 | −31.6 | −2.6 |

TABLE 3

| Treatment material | Experimental group | | | | | | | Comparison group |
|---|---|---|---|---|---|---|---|---|
| | VC | V2 | V4 | R2 | R4 | R6 | R7 | Dexibuprofen |
| Change in Murf1 gene expression relative to control group (%) | −4.2 | −2.4 | −8.5 | −9.9 | −13.7 | −17.5 | −24.1 | −3.3 |

FIGS. 3 and 4 are graphs showing relative amounts of the gene (mRNA) expression of Atrogin1 and Murf1 of experimental group, control group (Dex) and comparison group (dexibuprofen) relative to normal myocyte (control). Tables 2 and 3 show change in the Atrogin1 and Murf1 gene (mRNA) expression of the experimental group and the comparison group relative to the control group.

Referring to FIGS. 3 and 4, it is confirmed that the Atrogin1 and Murf1 genes were overexpressed in the control group treated with the dexamethasone compared to the normal myocyte. Compared with the control group, it is exhibited that the expression levels of the Atrogin1 and Murf1 genes are reduced overall in the experimental group further treated with the bean leaf extract.

Specifically, as shown in Table 2 above, the expression level of the gene of Atrogin1 in the experimental group treated with the extract of bean leaf at stage R2 to R7 is significantly reduced by 8.2 to 31.6% in comparison with the control group, and especially, such reduction is very effective in experimental group treated with extract of bean leaf at stage R7.

In addition, as shown in Table 3 above, the expression level of the gene of Murf1 in the experimental group treated with the extract of bean leaf at stage V4 to R7 is significantly reduced by 8.5 to 24.1% in comparison with the control group, and especially, such reduction is very effective in experimental group treated with extract of bean leaf at stage R7.

Meanwhile, it can be seen that in the comparison group treated with the dexibuprofen, the expression inhibition effects of the Atrogin1 and Murf1 genes are insignificant, and thus, general muscle pain suppressing substances are not suitable for inhibition or prevention of muscle loss, and their mechanisms of action are also different.

From the above results, it is expected that since the composition containing the bean leaf extract of the present invention as an active ingredient has excellent efficacy in the inhibition and prevention of myopathy, it is highly likely to be industrially applicable in various forms such as food, pharmaceutical or cosmetic composition.

The invention claimed is:

1. A method for inhibiting a myopathy comprising:
    administering a composition comprising a bean leaf extract as an active ingredient to a subject in need thereof,
    wherein,
    the bean leaf extract is an extract of bean leaf at stage R6, R7 or R8 during the growth stage of bean;
    the bean is selected from the group consisting of *Rhynchosia Nolubilis, Glycine max* (L.) Merr., *Vicia faba, Phaseolus vulgaris, Phaseolus vulgaris* L., *Vigna angularis, Phaseolus angularis* W. F. WIGHT., *Pisum sativum* L., *Glycine max* MERR, and a mixture thereof; and
    the myopathy is selected from the group consisting of sarcopenia, muscle loss and amyotrophic diseases.

2. The method according to claim 1, wherein the myopathy is senile myopathy.

3. The method according to claim 1, wherein the composition increases cell activity of myocyte.

4. The method according to claim 1, wherein the composition inhibits expression or activity of ubiquitin ligase of skeletal muscle.

5. The method according to claim 1, wherein the composition inhibits expression of Atrogin1 or Murf1 gene.

6. The method according to claim 1, wherein the extract of bean leaf is an extract of bean leaf at stage R7 during the growth stage of bean.

7. The method according to claim 1, wherein the composition is food composition, a pharmaceutical composition or a cosmetic composition.

8. The method according to claim 7, wherein the pharmaceutical composition is an oral formulation.

\* \* \* \* \*